US012029514B2

(12) United States Patent
Gonenc et al.

(10) Patent No.: US 12,029,514 B2
(45) Date of Patent: *Jul. 9, 2024

(54) REMOTE CENTER OF MOTION CONTROL FOR A SURGICAL ROBOT

(71) Applicant: Verb Surgical Inc., Santa Clara, CA (US)

(72) Inventors: Berk Gonenc, Santa Clara, CA (US); Yiming Xu, Santa Clara, CA (US); Margaret Nicholson, Santa Clara, CA (US); Pablo Garcia Kilroy, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,907

(22) Filed: Dec. 6, 2022

(65) Prior Publication Data

US 2023/0106256 A1    Apr. 6, 2023

Related U.S. Application Data

(63) Continuation of application No. 16/858,010, filed on Apr. 24, 2020, now Pat. No. 11,571,267.

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/37* (2016.02); *A61B 34/71* (2016.02); *A61B 34/77* (2016.02);
(Continued)

(58) Field of Classification Search
CPC ......... A61B 34/35; A61B 34/37; A61B 34/71; A61B 34/77; A61B 2562/02; A61B 34/74;
(Continued)

(56) References Cited

U.S. PATENT DOCUMENTS

| 5,397,323 A | 3/1995 | Taylor |
| 2012/0132018 A1 | 5/2012 | Tang |

(Continued)

FOREIGN PATENT DOCUMENTS

| JP | 2017512545 A | 5/2017 |
| KR | 101413406 B1 | 6/2014 |

(Continued)

OTHER PUBLICATIONS

Fontanelli, Giuseppe Andrea, et al. "A novel force sensing integrated into the trocar for minimally invasive robotic surgery." 2017 IEEE/RSJ International Conference on Intelligent Robots and Systems (IROS). IEEE, 2017.

(Continued)

*Primary Examiner* — Abby Y Lin
*Assistant Examiner* — Danielle M Jackson
(74) *Attorney, Agent, or Firm* — Lempia Summerfield Katz LLC (57) ABSTRACT

For control about a remote center of motion (RCM) of a surgical robotic system, possible configurations of a robotic manipulator are searched to find the configuration providing a greatest overlap of the workspace of the surgical instrument with the target anatomy. The force at the RCM may be measured, such as with one or more sensors on the cannula or in an adaptor connecting the robotic manipulator to the cannula. The measured force is used to determine a change in the RCM to minimize the force exerted on the patient at the RCM. Given this change, the configuration of the robotic (Continued)

manipulator may be dynamically updated. Various aspects of this RCM control may be used alone or in combination, such as to optimize the alignment of workspace to the target anatomy, to minimize force at the RCM, and/or to dynamically control the robotic manipulator configuration based on workspace alignment and force measurement.

17 Claims, 5 Drawing Sheets

(51) Int. Cl.
  A61B 34/37 (2016.01)
  B25J 9/00 (2006.01)
  B25J 9/16 (2006.01)
(52) U.S. Cl.
  CPC ........... B25J 9/0096 (2013.01); B25J 9/1633 (2013.01); B25J 9/1689 (2013.01); A61B 2562/02 (2013.01)
(58) Field of Classification Search
  CPC .............. A61B 2090/064; A61B 34/76; A61B 2090/065; A61B 34/70; A61B 90/06; B25J 9/0096; B25J 9/1633; B25J 9/1689
  See application file for complete search history.

(56) References Cited

U.S. PATENT DOCUMENTS

| | | |
|---|---|---|
| 2012/0191107 A1 | 7/2012 | Tanner |
| 2017/0105811 A1 | 4/2017 | Garbus |
| 2017/0333275 A1* | 11/2017 | Itkowitz ................. A61G 13/02 |
| 2019/0053824 A1 | 2/2019 | Scheib |
| 2019/0105118 A1 | 4/2019 | Itkowitz et al. |
| 2019/0192254 A1 | 6/2019 | Garbus |
| 2020/0107896 A1 | 4/2020 | Thompson |
| 2020/0268479 A1 | 8/2020 | Garbus |
| 2020/0315721 A1 | 10/2020 | Rabindran et al. |
| 2020/0345438 A1 | 11/2020 | Stricko, III et al. |
| 2021/0008710 A1 | 1/2021 | Kiyosawa |
| 2021/0045817 A1* | 2/2021 | Koenig ...................... B25J 9/12 |
| 2021/0128262 A1 | 5/2021 | Gomez |
| 2021/0290320 A1 | 9/2021 | Mao et al. |
| 2021/0298850 A1* | 9/2021 | Huang ................... A61B 34/35 |
| 2021/0330351 A1 | 10/2021 | Scheib |
| 2021/0401538 A1 | 12/2021 | Garbus |
| 2022/0054209 A1 | 2/2022 | Lim et al. |
| 2022/0079695 A1 | 3/2022 | Thompson |
| 2023/0329836 A1 | 10/2023 | Garbus |
| 2023/0363840 A1 | 11/2023 | Thompson |

FOREIGN PATENT DOCUMENTS

| | | |
|---|---|---|
| KR | 20180097633 A | 8/2018 |
| WO | 2015142814 A1 | 9/2015 |
| WO | 2018147930 A1 | 8/2018 |
| WO | 2019040531 A1 | 2/2019 |

OTHER PUBLICATIONS

Trejos, A. L., R. V. Patel, and M. D. Naish. "Force sensing and its application in minimally invasive surgery and therapy: a survey." Proceedings of the Institution of Mechanical Engineers, Part C: Journal of Mechanical Engineering Science 224.7 (2010): 1435-1454.

Li, Temei; Payandeh, Shahram; "Design of spherical parallel mechanisms for application to laparoscopic surgery"; Robotica, vol. 20, Issue 2, Mar. 2002, pp. 133-138 (Year: 2002).

Scurtu, I. L., et al. "Kinematics and workspace of a new surgical robot with five degrees of freedom." Proceedings of 2012 IEEE International Conference on Automation, Quality and Testing, Robotics. IEEE, 2012.

European Search Report for Application No. EP 20 93 1989 mailed Nov. 27, 2023.

* cited by examiner

REMOTE CENTER OF MOTION CONTROL FOR A SURGICAL ROBOT

RELATED APPLICATION

This application is a continuation of U.S. application Ser. No. 16/858,010, filed Apr. 24, 2020, which is hereby incorporated by reference in its entirety

BACKGROUND

The present embodiments relate to robotic systems for minimally invasive surgery (MIS). MIS may be performed with robotic systems that include one or more robotic manipulators for manipulating surgical tools based on commands from a remote operator. A robotic manipulator may, for example, support at its distal end various surgical instruments and devices, including scalpels, clamps, scissors, and imaging devices (e.g., endoscope). Using the robotic system, the surgeon controls the robotic manipulators in teleoperation during MIS.

The surgical instruments and devices are inserted into the body of the patient via cannulas. By hardware or software design, the robotic manipulator has a remote center of motion (RCM) that is stationary relative to the base of the robotic manipulator and thus to the patient. To avoid injury to the patient, the RCM is aligned with the insertion point on the cannula. The robotic manipulator has a confined workspace, which describes the patient volume inside which the surgical instrument tip can reach and operate. Using a redundant robotic manipulator (e.g., more than 6 joints), there exist several different configurations in which the robotic manipulator can be docked to a cannula. As the configuration of the robot arm changes while maintaining the RCM, the workspace also moves. Among these configurations, one may be preferable over the others to ensure that most or all of the target anatomy falls within the operable workspace. Unnecessary trauma may be caused to a patient should it be discovered after cannula placement that the instrument does not reach the target anatomy. It is important to bring the robotic manipulator(s) to a proper configuration where the target anatomy is within reach of the surgical instrument in the shortest possible time and not extend the patient's time under anesthesia.

Once docked to the cannula, the robotic manipulator is not necessarily at an "optimal" configuration ensuring that the target anatomy is in its workspace. The "non-optimal" configuration of the robotic manipulator relative to the target anatomy may be due to the docking process. The target anatomy may also be redefined during the operation. Under these circumstances, the robotic manipulator may need to be reconfigured to align the workspace with the target anatomy. The reconfiguration may be by moving various joints of the manipulator around the fixed insertion port to coincide the workspace with the target anatomy. Manually reconfiguring (1) takes significant mental effort to visualize the shape and motion of the workspace as the arms are moved and (2) takes physical effort as multiple joints of the robotic manipulator may need to be moved one-by-one. Multiple adjustments may be needed due to complex mechanical structure before reaching the desired configuration, all of which expend valuable intraoperative time. In a complex robotic system with several degrees of freedom, it is difficult to visualize the workspace of the robot, especially exactly how the configuration determines the workspace.

SUMMARY

By way of introduction, the preferred embodiments described below include methods, systems, instructions, and computer readable media for RCM control of a surgical robotic system. Given an RCM, possible configurations of a robotic manipulator are searched to find the configuration providing a greatest overlap of the workspace of the surgical instrument with the target anatomy. The force at the RCM may be measured, such as with one or more sensors on the cannula or in an adaptor connecting the robotic manipulator to the cannula. The measured force is used to determine a change in the RCM to minimize the force exerted on the patient at the RCM. Given this change, the configuration of the robotic manipulator may be dynamically updated. Various aspects of this RCM control may be used alone or in combination, such as to optimize the alignment of workspace to the target anatomy, to minimize force at the RCM, and/or to dynamically control the robotic manipulator configuration based on workspace alignment and force measurement.

In a first aspect, a method is provided for RCM control of a surgical robotic system. An RCM is established for a robotic manipulator. An amount of overlap between a target anatomy and each of a plurality of workspaces of a surgical instrument on the robotic manipulator is determined. The workspaces correspond to different configurations of the robotic manipulator about the RCM. The configuration of the robotic manipulator with a greatest of the amount of overlap is selected. The robotic manipulator joints are moved to new positions corresponding to the selected configuration.

In a second aspect, a method is provided for RCM control of a surgical robotic system. A force at the RCM is measured. The robotic manipulator configuration is adjusted to reduce the force exertion at the RCM and to maintain an overlap between the workspace of the surgical instrument and a target anatomy in the patient.

In a third aspect, a surgical robotic system is provided for medical teleoperation. A surgical instrument connects to a robotic manipulator. An adaptor connects to the robotic manipulator. The adaptor is configured to connect with a cannula during teleoperation. One or more force sensors are on the adaptor. A controller is configured to adjust a RCM of the robotic manipulator based on output from the force sensor.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Assisted arm manipulation is provided for repositioning the remote center of motion (RCM). The RCM may be safely, easily, and quickly repositioned or maintained so that the overlapping volume between the target anatomy and a workspace of a robotic manipulator (e.g., robotic arm) and surgical instrument is maximized. Possible robotic manipulator configurations are tested to identify an optimal level of overlap given a position of the RCM. The robotic manipulator may be moved to account for this alignment, repositioning the RCM, and/or teleoperation.

Cannula (e.g., trocar) force (e.g., translational, pressure, and/or torque) measurement may be used for adaptive RCM control. The RCM may be moved to adapt to patient motion, motion of the robotic manipulator, or another source of undesired force on the tissue of the patient at the insertion (i.e., RCM is at the entry location into the patient). In one embodiment, the force is measured with a sensor on the cannula. In another embodiment, the force exerted on the cannula is measured using sensors at the contacting points with the adapter of the robotic manipulator. Information about the force and stress at the cannula insertion point through the abdomen wall is provided by the measurements at the adaptor, assisting the user or controller to adjust the position of the RCM accordingly and to release excessive stress on the abdomen wall as needed.

Figure 1:
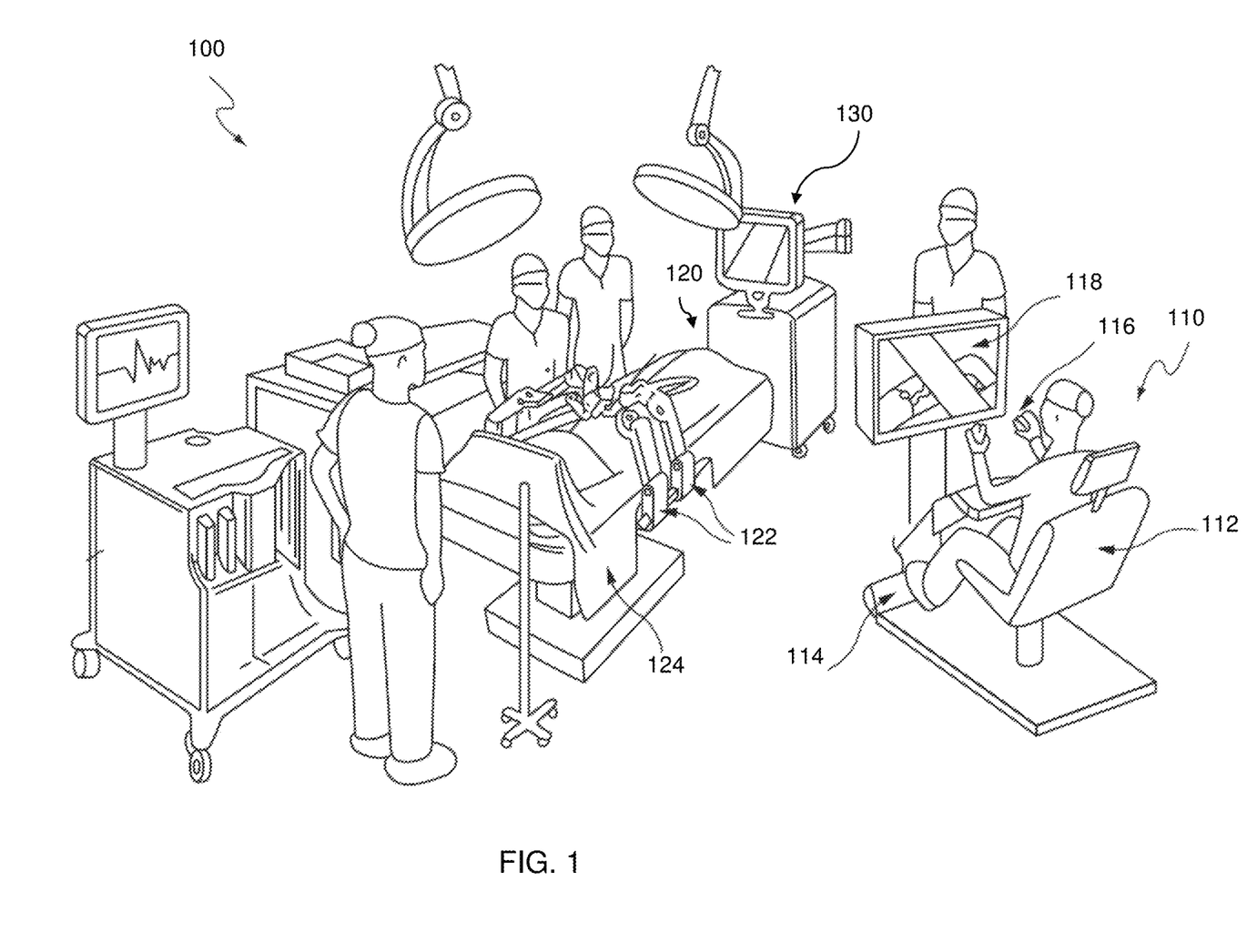
FIG. 1 is an illustration of one embodiment of an operating room environment with a surgical robotic system according to one embodiment.
Figure 2:
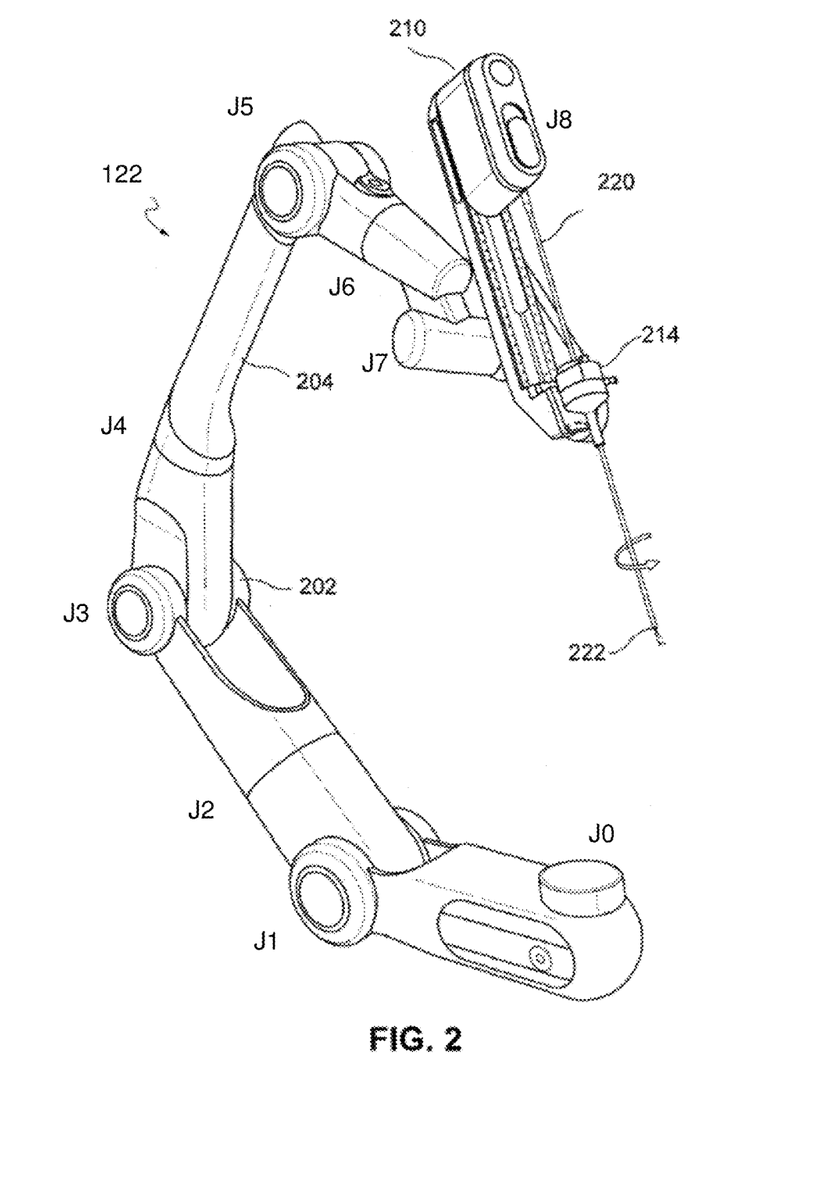
FIG. 2 illustrates an example surgical robot arm and surgical tool.

FIGS. 1 and 2 show an example surgical robotic system. The approaches for RCM control are discussed below in reference to this example system. Other surgical robotic systems and surgical robots or non-surgical robotic systems and robots may use the approaches.

Figure 5:
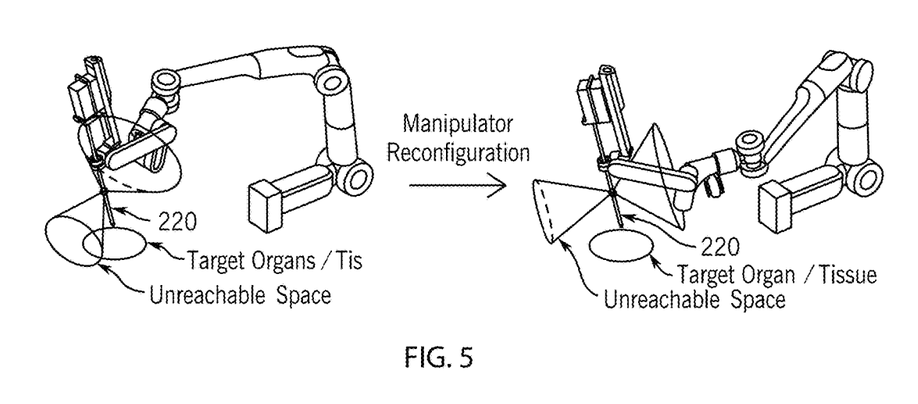
FIG. 5 illustrates example workspace alignment with target anatomy.
Figure 6:
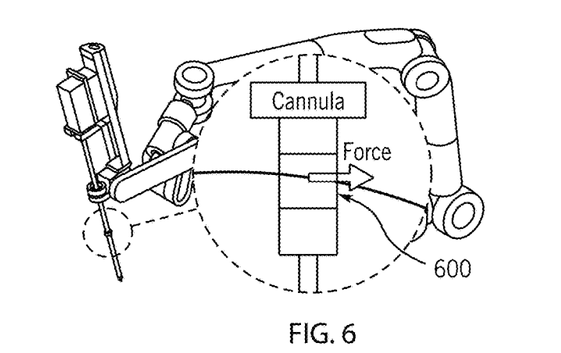
FIG. 6 illustrates example workspace alignment while also including force sensing at the remote center of motion.
Figure 7:
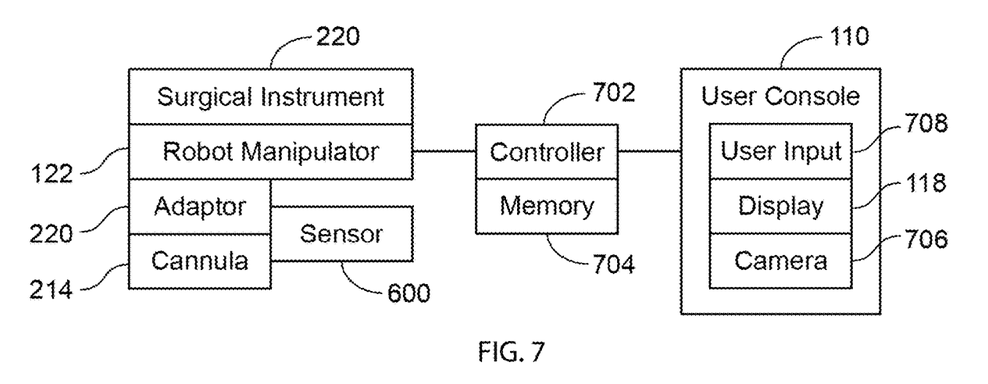
FIG. 7 is a block diagram of one embodiment of a surgical robotic system.

FIGS. 3-6 are directed to RCM control, including workspace alignment with the target anatomy and/or force sensing on the adaptor. FIG. 7 is directed to a system for RCM control.

FIG. 1 is a diagram illustrating an example operating room environment with a surgical robotic system 100 for which commands from the user are converted into motion of the surgical robotic manipulators 122 with iterative inverse kinematics. The surgical robotic system 100 includes a user console 110, a control tower 130, and a surgical robot 120 having one or more surgical robotic manipulators 122 mounted on a surgical platform 124 (e.g., a table or a bed etc.), where surgical tools with end effectors are attached to the distal ends of the robotic manipulators 122 for executing a surgical procedure. Additional, different, or fewer components may be provided, such as combining the control tower 130 with the console 110 or surgical robot 120. The robotic manipulators 122 are shown as table-mounted, but in other configurations, the robotic manipulators 122 may be mounted in a cart, a ceiling, a sidewall, or other suitable support surfaces.

Generally, a user, such as a surgeon or other operator, may be seated at the user console 110 to remotely manipulate the robotic manipulators 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may include a seat 112, pedals 114, one or more handheld user interface devices (U IDs) 116, and an open display 118 configured to display, for example, a view of the surgical site inside a patient and graphic user interface. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. The user inputs commands for the movement of the surgical manipulators 122 and/or end effectors. This user control determines position, the rate of movement, and the change in rate of movement of the robotic manipulators 122. The rate and change in rate result in dynamic torque expected to be provided by the robotic manipulators 122. The surgeon sitting in the seat 112 may view and interact with the display 118 to input commands for movement in teleoperation of the robotic manipulators 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery using teleoperation. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic manipulators 122. Some surgical tasks, such as retracting, suturing, or other tissue manipulation, may instead be performed by one or more robotic manipulators 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input commands from the user console 110 to robotic control commands and transmit the control commands to the surgical robot 120. The control tower 130 performs iterative inverse kinematics. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including cannula placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other cannulas. After insufflation, if required, manual instruments can be inserted through the sleeve to perform any laparoscopic steps by hand.

Next, the surgical team may position the robotic arms 122 over the patient and attach each arm 122 to a corresponding sleeve (e.g., cannula). The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master U IDs 116 and foot pedals 114. The patient-side assistant can attach and detach the tools, as required, throughout the procedure. The surgeon seated at the user console 110 can begin to perform surgery as teleoperation using the tools controlled by two master U IDs 116 and foot pedals 114. The system translates the surgeon's hand, wrist, and finger movements through the master U IDs 116 into precise real-time movements of the surgical tools. Therefore in direct teleoperation, the system constantly monitors every surgical maneuver of the surgeon and pauses instrument movement if the system is unable to precisely mirror the surgeon's hand motions. In case the endoscope is moved from one arm to another during surgery, the system can adjust the master U IDs 116 for instrument alignment and continue instrument control and motion. The foot pedals 114 may be used to activate various system modes, such as endoscope control and various instrument functions including monopolar and bipolar cautery, without involving surgeon's hands removed from the master U IDs 116.

FIG. 2 is a schematic diagram illustrating one exemplary design of a robotic manipulator, a tool drive, and a connector loaded with a robotic surgical tool, in accordance with aspects of the subject technology. As shown in FIG. 2, the example surgical robotic manipulator 122 may include a plurality of links (e.g., a link 202) and a plurality of actuated joint modules (e.g., a joint 204, see also joints J1-8) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 122. The tool drive 210 may include a cannula 214 coupled to its end to receive and guide a surgical instrument or end effector 220 (e.g., endoscopes, staplers, scalpel, scissors, clamp, retractor, etc.). The surgical instrument (or "tool") 220 may include an end effector 222 at the distal end of the tool. The plurality of the joint modules of the robotic manipulator 122 can be actuated to position and orient the tool drive 210, which actuates the end effector 222 for robotic surgeries. The end effector 222 is at a tool shaft end. In other embodiments, the tool shaft end is a tip of a needle or other object.

In the example of FIG. 2, the joint J0 is a table pivot joint and resides under the surgical table top. Joint J0 is nominally held in place during surgery. Joints J1 to J5 form a setup or Cartesian arm and are nominally held in place during surgery, so do not contribute to motion during surgical teleoperation. Joints J6 and J7 form a spherical arm that may actively move during surgery or teleoperation. Joint J8 translates the tool 220, such as the end effector 222, as part of a tool driver. Joint J8 may actively move during surgery. Joints J6-8 actively position a tool shaft end (i.e., end effector 222) during surgery while maintaining an entry point into the patient at a fixed or stable location (i.e., RCM) to avoid stress on the skin of the patient. During set-up, any of the joints J0-J8 may move. During surgery, the joints J6-8 may move subject to hardware or safety limitations on position, velocity, acceleration, and/or torque. The surgical tool 220 may include none, one, or more (e.g., three) joints, such as a joint for tool rotation plus any number of additional joints (e.g., wrists, rotation about a longitudinal axis, or other type of motion). Any number of degrees of freedom may be provided, such as the three degrees from the joints J6-8 and none, one, or more degrees from the surgical tool 220.

Figure 3:
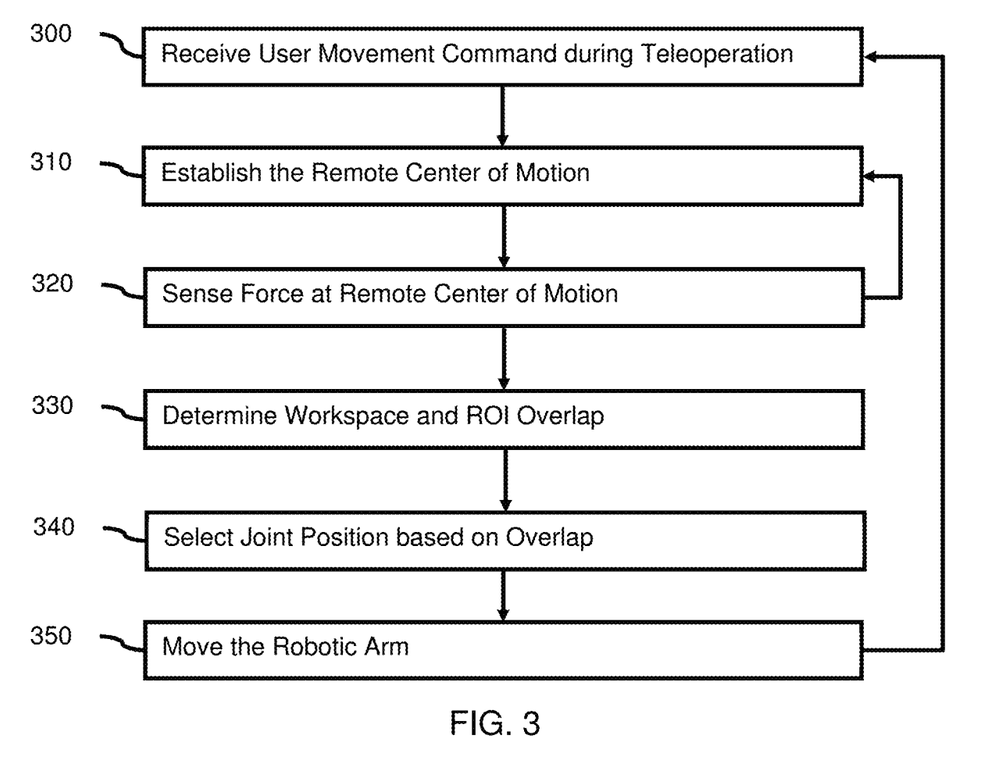
FIG. 3 is a flow chart diagram of one embodiment of a method for remote center of motion control of a surgical robotic system.

FIG. 3 is a flow chart diagram of one embodiment of a method for remote center of motion control of a surgical robotic system. The workspace of the end effector 222 of the surgical instrument 220 is aligned with the target anatomy in a way considering the various options for positioning of the robotic arm 122. The alignment may account for repositioning of the RCM during teleoperation. The RCM may be repositioned based on force sensing, such as sensing using sensors in the adaptor of the robotic manipulator for connecting with the cannula 214.

The method of FIG. 3 is implemented by a control processor, such as the control tower 130, computer, workstation, sever, or another processor. Any computer of the surgical robotic system 100 may be used. A user interface provides the movement commands from the user received in act 300. The control processor (e.g., controller) establishes the RCM in act 310, determines the overlap in act 330, and selects joint position in act 340. A force sensor, such as a torque or pressure sensor, senses force in act 320. The robotic arm 122 and/or surgical tool 220 are moved using the instructions or control from the control processor in act 350. Other devices may perform and/or be used in any of the acts.

The acts are performed in the order shown or other orders. For example, act 300 is performed after any of the other acts. As another example, act 320 is performed before or after any of the acts.

Additional, different, or fewer acts may be used. For example, act 300 is not provided where the alignment is performed prior to teleoperation. As another example, act 320 is not performed, such as where workspace alignment is performed without dynamic change in the RCM (e.g., alignment prior to teleoperation and/or movement by the patient). In another example, acts 330 and 340 are not provided where force sensing on the adaptor is used to control RCM without considering workspace alignment. In another example, acts for initially positioning the surgical tool 220 in the patient, planning surgery, and/or removing the surgical tool 220 from the patient may be provided.

In act 300, the control processor receives a user command to move the robotic manipulator 122 or surgical tool 220 of the robotic manipulator 122 prior to or during the teleoperation on a patient. The user input is received from the user console 110, such as the pedals 114 or user interface devices 116, via wireless or wired interface by the control processor. In other embodiments, the user commands are received by loading from memory or transmission over a computer network.

In preparation for teleoperation, the user sits down at the surgeon console 110. After positioning of the robotic manipulator 122 for teleoperation, one or more joints are locked in place with a RCM at the patient skin or incision entry point. For example, joints J0-J5 (see FIG. 2) are locked. The locking is by a brake and/or avoiding energizing the motors for the joints. These joints remain locked during teleoperation. Any of joints J0-J5 may be unlocked and moved to change the RCM.

During teleoperation, the user enters commands to move the robotic manipulator 122 and/or surgical tool 220. The commands are for motion. Different commands may be provided for different movements. The commands may be for movement of the end effector 222. These commands may not be for movement of particular joints. The control processor converts the movement commands to controls of particular joints of the robotic manipulator 122 and/or surgical tool 220.

In act 310, the control processor establishes the RCM for the robotic manipulator 122. While preparing for the surgery, a table-side assistant inserts the cannula 214 through the patient's abdomen wall. The robot manipulator 122 is docked to the cannula 214. An adaptor of the robotic manipulator 122 connects to the cannula 214. Docking is carefully performed to avoid excessive force exertion on the abdomen ports. After the robot manipulators 122 are docked, the RCM is set at the point of insertion. The spatial relationship of the adaptor in the robotic manipulator frame of reference to the cannula 214 is known. Upon connection of the adaptor to the cannula 214, the RCM at the point of insertion along the cannula 214 is set as the RCM.

The surgical robot 120 will perform the operation while maintaining the RCM at the fixed position. Without motion of the RCM, the robotic manipulator 122 continues to operate with the RCM in one location and without risk of harm to the tissue of the patient.

Due to patient motion, motion of the robotic manipulator, and/or another source of motion, the RCM may be moved. During the operation, the abdomen position may change for various reasons. The operation may involve several phases where the patient may be positioned and oriented differently by adjusting the height and inclination of the table. Because the relative positions of the abdomen openings may be shifting, maintaining a fixed RCM position could introduce additional stress on the patient's abdomen and may lead to unnecessary trauma or injuries. The robotic manipulator 122 accounts for the shift or motion by moving the RCM to avoid harm to the tissue of the patient.

The RCM is established at a new location in the coordinate system of the robotic manipulator 122. To avoid having to release and redock the robotic arm 122 from the cannula 214, the RCM shifts or changes based on a measured force at the RCM (i.e., at the insertion location into the patient). A force, such as a pressure or torque, is measured at or for the RCM in act 320. The force is measured in any number of degrees of freedom, such as measuring force in two degrees of freedom along a plane tangential to the patient at the insertion point or measuring in six degrees of freedom to account for three translational and three rotational forces (or torques). The force at the RCM after docking and/or during teleoperation by the robotic manipulator 122 and the surgical instrument 220 is sensed. The force sensing may enable the robotic system 120 to issue warnings and to assist RCM adjustments to minimize stress or force on the patient's abdomen. The force sensing may be used for automatic adjustment of the RCM. The feedback from act 320 to act 310 shows using the force to reposition the RCM.

In one embodiment, the force is sensed in act 320 with one or more sensors on the cannula 214. FIG. 6 shows a force sensor 600 for sensing force of the cannula 214 (e.g., trocar) on the patient tissue. Since the cannula 214 connects to the robotic manipulator 122 after docking, relative motion between the patient and the robotic manipulator 122 causes force on the cannula 214 by the patient tissue. The presence of injurious forces at the insertion port can be checked by integrating the sensor 600 onto the cannula shaft to measure strain at the incision site.

The sensor 600 is a force gauge, such as a thin capacitive or resistive sensor. Due to a thin and flexible structure, the sensor 600 may be wrapped around the cannula shaft. Once docked to the robotic manipulator 122, the electrical connection of the control processor to the sensor 600 is established through the docking site (i.e., adaptor) so that the force sensor is turned on. Other connections, such as wireless connection or cabled connection, may be used. The readings of the sensor 600 provide a direct measure (e.g., continuous real-time monitoring) of force magnitude and/or direction at the tool insertion site. If the magnitude of forces sensed by the integrated sensor 600 exceeds a predefined safety threshold (e.g., forces that may cause injury), a desired RCM motion is computed to shift the RCM, rather than keeping the RCM fixed.

Figure 4A:
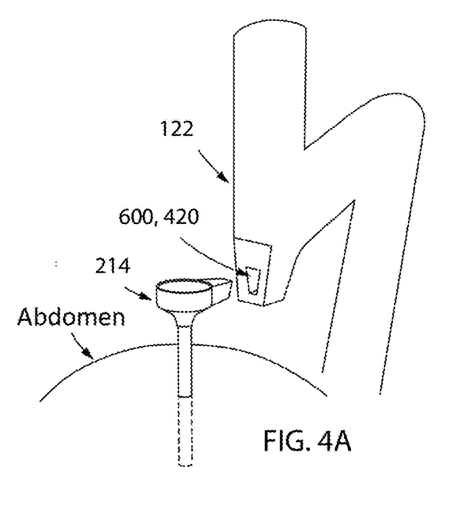
FIGS. 4A and 4B show an example adaptor and sensor for connecting with a cannula.
Figure 4B:
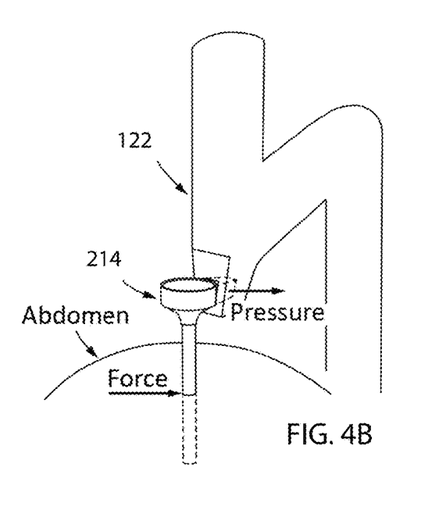

In another embodiment, the sensor 600 is in an adaptor 420 of the robotic manipulator 122. FIGS. 4A and 4B show an example. The adaptor 420 is configured to connect the robotic manipulator 122 to the cannula 214. For example, the adaptor 420 is a recess or female connector shaped to allow connection in a fixed orientation, such as a cuboid having a trapezoid shape. Other keyed shapes may be used. Alternatively, the adaptor 420 is a male connector formed as a keyed extension. A snap fit, pressure fit, motorized lock, and/or mechanical latch may be provided to lock the adaptor 420 to the cannula 214 for docking.

The forces (e.g., lateral force and/or torque) at the contacting points on the cannula adapter 420 of the robotic manipulator 122 are measured in act 320. Sensing at the adaptor 420 may avoid the design difficulties and sterilization concerns of placing sensors 600 directly on the cannula 214.

The sensor 600 may be any type of sensors to correlate the force from the abdomen. For example, pressure, strain, force, or proximity sensors may be used. The sensor 600 may be formed from multiple sensors, such as using a plurality of one-degree of freedom sensors. The sensor senses force in one direction or rotation. By using different sensors in different positions within or on the adaptor 420, forces in different, multiple degrees of freedom are measured. For example, pressure sensors are positioned on five surfaces in the adaptor corresponding to the five surfaces forming the keyed shape. The surfaces of the adaptor 420 that contact the cannula 214 when connected each have a sensor. Fewer or more sensors may be provided.

In the example of FIGS. 4A and 4B, the pressure sensors are inside the distal cannula adapter 420. The sensors are placed on the robot manipulator 122 and underneath the sterile drape in order to minimize the risk of contamination and potential damages to the sensors. As the robot manipulator 122 gets docked to the cannula 214 (see FIG. 4A), the sensor arrangement covers all possible directions of pressure originated from the stress on the abdomen wall. Given the known spatial relationship of the adaptor 420 to the cannula 214, the sensed forces at the adaptor 420 may be geometrically related to the force at the insertion point (see FIG. 4B). The measurements from the sensors are calibrated, based on the type and geometry of the cannula 214, to eliminate the nominal pressure from the docking mechanism and to correlate the additional pressure readings to the forces on the abdomen wall.

Diagrams of the force direction and magnitude may be displayed to the user. Robotic manipulator 122 adjustment may be performed automatically, semi-automatically, or manually by the user to minimize the force on the abdomen. In cases when the forces rise above a safety threshold, warnings may be issued to the user.

Referring again to FIG. 3, in act 330, the control processor determines an amount of overlap between a target anatomy and each of a plurality of workspaces of the surgical instrument 220 on the robotic manipulator 122. The robotic manipulator 122 and/or surgical instrument 220 may be configured (i.e., the joint angles set) in various possible ways. For example, at the RCM, the joint J6, a spherical roll joint, may have various positions discretized over any range and any number of steps within the range. At each possible position, a workspace volume is provided for the end effector 222 or the surgical instrument 220. The robotic manipulator 122 and surgical instrument 220 may be moved and operate within the particular workspace volume. Each position of the joint J6 or other robot configuration provides the workspace at a different relative location (e.g., different translated and/or rotated).

Based on the configuration of the robotic manipulator 122, the control processor computes the accessible workspace of the end effector 222. For example, the workspace is a sphere around the RCM point with some unreachable conical cuts inside. FIGS. 5 and 6 shows the workspace as a shaded sphere with a conical region which the end effector 222 cannot reach. If the origin of the J6 joint (spherical roll) is translated by keeping the RCM fixed, the workspace will rotate about its center. The conical region rotates to different positions relative to the patient. If the RCM is moved, then the workspace will shift in space as well.

For workspace alignment, the target anatomy is determined in the coordinate system of the robotic manipulator 122. The surgeon manually, or the imaging system automatically, defines the boundaries of the target anatomy. Intraoperative or pre-operative imaging may be used to segment the region of interest for the teleoperation, such as identifying an organ, lesion, or part of anatomy. X-ray, computed tomography, ultrasound, or magnetic resonance imaging may be used. In another embodiment, an endoscopic view and the surgeon's knowledge of human anatomy are used.

Using calibration, an imaging detector mounted at a known spatial location relative to the robotic manipulator 122 (e.g., imaging with endoscope on a robotic manipulator 122), and/or detection of part of the robotic manipulator 122 or surgical instrument 220 in the imaging, the coordinate systems for the imaging and the robotic surgical system 120 are aligned or registered. The target anatomy may be located in the coordinate system of the robotic manipulator 122.

The overlap of the volume or other region of the target anatomy with the workspace is optimized. Various workspaces are possible, corresponding to different positions of the robotic manipulator 122 about the RCM. Before or during teleoperation, after the robotic manipulator 122 is docked, optimal joint angles may be computed to maximize the volumetric overlap of the surgical tool's workspace and the target organ/tissue while holding RCM point fixed (i.e., constrained optimization). The possible workspaces in the example using joint J6 have different orientation of the workspace (no translation) so that the unreachable zones (the conical cuts in the workspace) are maintained outside of the target tissue/organ to a maximum extent.

The amount of overlap of the possible workspaces (i.e., workspace oriented over the range of configurations) with the volume of the target anatomy is determined. The volume, area, and/or distance of the spatial overlap of the workspace and the target anatomy is calculated. The amount of overlap may be different for different possible configurations, such as different orientations over the discretized range of joint positions for a spherical roll joint. Due to different possible configurations, the workspace may be translated and/or rotated while maintaining the RCM.

The different possible workspace orientations and/or positions are searched to find the greatest amount of overlap. The amount of overlap for each possible workspace with the target anatomy is determined. After the robotic manipulator 122 is docked to the cannula 214, the control processor scans or searches through a discretized neighborhood of the configurations (e.g., J6 (spherical roll) joint positions) and computes the overlapping volumes of the workspace corresponding to each configuration (e.g., movement of J6 origin within the specified neighborhood) with the target anatomy. The configuration that provides the maximum overlap is selected as the "optimal configuration."

Rather than searching all possible workspaces, a nonlinear search may be used. Instead of the linear search, nonlinear optimization methods, such as simulated annealing or a coarse-to-fine search, may be used to speed up the search. In order to obtain the optimal pose quickly, the search may be done locally, assuming that the initial manipulator configuration is already close to an optimum. This may lead to a search result that may suggest "fine-tuning" of the manipulator configuration rather than a gross-repositioning.

The determination of the configuration to maximize overlap is performed once the RCM is established (e.g., after docking). This determination may occur prior to teleoperation. The determination may be repeated. The determination may occur for each change in the RCM during teleoperation. The determination may occur as the target anatomy shifts, such as through staged operation on different anatomy. The determination may occur due to a change in the surgical tool 220 or for any other reason where the target anatomy or workspace shifts or changes.

In act 340, the control processor selects the position of the robotic manipulator with a greatest of the amount of overlap. The configuration for the possible workspace that provides the most overlap with the target anatomy is selected. FIG. 5 shows an example. The workspace orientation on the left shows part of the target anatomy being outside the workspace sphere, such as in the conical cut-out. The workspace orientation on the right shows the workspace sphere rotated so that none of the target anatomy is outside of the workspace (i.e., conical cut-out is rotated to not intersect the target anatomy). The configuration of the robotic manipulator 122 (e.g., rotation angle of joint J6) is selected to provide the greatest overlap.

Such selection is repeated during teleoperation. The same or different configuration is selected for each repetition. Due to positional shifts, more or less maximum overlap may be provided. Due to positional shifts, a different configuration may provide greater overlap than the previous configuration providing greatest overlap. A different one of the possible workspaces and corresponding configuration is selected.

In act 350, the control processor moves the robotic manipulator 122 to the selected position or configuration. The control processor causes movement of the robotic manipulator 122 and/or the surgical tool 220. The output movement commands for the active joints for docking and/or during teleoperation cause the joints to change position. The robotic manipulator 122 is moved to be in the selected configuration.

In one example using the joint J6, the selection of act 340 provides a target x and y movement of the joint J6 (spherical roll, sr) origin, which target provides the optimal pose (i.e., maximum overlap of the robot workspace and the target anatomy): $w_{x,sr}$, $w_{y,sr}$. The robotic manipulator 122 is moved to this optimal configuration ($q_{opt}$) while keeping the forces (and therefore strain) at the RCM at a safe level. If the robotic manipulator 122 was docked without pulling/pushing the cannula 214 and if the patient remains stationary, then a special case occurs where the force at the insertion port is small (thus safe) from the beginning, and the RCM is maintained fixed at this location. In case there are residual forces acting on the cannulas 214 after docking and/or due to another source, the strain is relieved by updating (i.e., sliding) the RCM position as well as optimizing the overlap.

The joint position or robotic manipulator 122 configuration may be selected in act 340 based on more than overlap. The selection may be based on the user commands in teleoperation, an adjustment of the RCM to reduce the force, and/or an amount of overlap of a workspace of the surgical instrument 220 with a region of interest in the patient (i.e., target anatomy). The configuration is selected in a way accounting for various concerns.

In one embodiment that accounts for possible RCM repositioning and overlap optimization with or without teleoperation commands, the readings of the sensor 600 provide a direct measure (e.g., continuous real-time monitoring) of force magnitude and direction at the tool insertion site for repositioning the RCM. If the magnitude of forces sensed exceed a predefined safety threshold (e.g., forces that may cause injury), a desired RCM motion is computed based on the magnitude, rather than keeping the RCM fixed. One example of this control is provided by:

if $(\text{norm}(\vec{F}_{sensed}) > (\vec{F}_{threshold})$, then $\vec{\Delta p}_{RCM} = {}_{J7}^{base}R * {}_{sensor}^{J7}R \dfrac{(\vec{F}_{sensed} - \vec{F}_{threshold})}{K}$, else $\vec{\Delta p}_{RCM} = \vec{0}$ where sensed is the sensed force vector, $\vec{F}_{threshold}$ is the threshold force vector, $\vec{\Delta p}_{RCM}$ is the change in position vector of the RCM, ${}_{J7}^{base}R$ is the 3×3 rotation matrix from robot base (world frame) to joint J7 (spherical pitch) frame, and ${}_{sensor}^{J7}R$ is the 3×3 rotation matrix from the joint J7 frame to the sensor's coordinate frame. The rotation matrix may dynamically change depending on the configuration of the robotic manipulator 122. ${}_{sensor}^{J7}R$ is a fixed registration since once the manipulator is docked, the orientation of the cannula 214 is fixed relative to the distal block attached to J7. K is a spring stiffness that defines how much translation is to be commanded to the robot to relieve a given force. A large K value lead to a "not-so-responsive" system. A small K value will generate a sensitive system trying to drop the force to the set safety threshold quickly. If the sensitive system is not well-tuned, overshooting, and thus oscillatory robot motion, may result.

FIG. 6 shows an example of both workspace alignment and shift in RCM for selection of the robot configuration for the robotic manipulator 220 of FIG. 2. During teleoperation, there may be excessive forces at the cannula 214, such as due to motion of the patient. To avoid injuries, the detected force F on the cannula 214 (sensed via embedded force sensors 600) is used to compute a new RCM position, $\vec{\Delta p}_{RCM}$, to relieve injurious stress at the insertion port. The optimal joint angles are recomputed under this new RCM constraint to reorient the workspace such that the target/tissue is still maintained to the maximum extent within the reachable workspace. The robotic manipulator 122 is moved by moving one or more joints according the overlap and the RCM repositioning with or without movement of the surgical instrument from an operator during teleoperation. The proximal wrist (J11), distal wrist (J10) and tool rotate joints (J9) of the surgical instrument 220 are not used if repositioning before teleoperation. In teleoperation, these joints (J9, J10 and J11) receive commands only for tool manipulation. For the spherical manipulator joints (J6, J7, J8), the computed incremental joint commands for overlap and RCM position are added to the command due to teleoperation of the surgeon so that the repositioning can take place continuously (even during the teleoperation).

The incremental joint movements to satisfy both the workspace requirement, i.e., the incremental movement of the spherical roll joint origin about the RCM point ($w_{x,sr}$, $w_{y,sr}$), and the insertion port force requirement (i.e., the displacement of the RCM point to relieve the excess force at the RCM ($\vec{\Delta p}_{RCM}$)) may be computed sequentially (e.g., reposition RCM, then optimize for overlap given the configuration possibilities at the new RCM position). Alternatively, the various motions can be used in one solution, such as given by:

$$J = \begin{bmatrix} J_{tr} \\ J_{RCM} & 0_{3\times 3} \\ J_{sr} & 0_{2\times 3} \end{bmatrix}$$

$$\vec{\Delta x} = \begin{bmatrix} \vec{\Delta p}_{tr} \\ \omega_{z,tr} \\ \vec{\Delta p}_{RCM} \\ \omega_{x,sr} \\ \omega_{y,sr} \end{bmatrix} = \begin{bmatrix} \vec{\Delta p}_{RCM} \\ 0 \\ \vec{\Delta p}_{RCM} \\ \omega_{x,sr} \\ \omega_{y,sr} \end{bmatrix}$$

$$\vec{\Delta q}_{repo} = \text{]}^{+} * \vec{\Delta x}$$

where ] denotes a combined Jacobian, ]$^+$ is the pseudoinverse of this combined Jacobian, x, y, z are spatial coordinates, tr is tool roll (J9) joint origin, and sr is spherical roll (J6) joint origin. The resulting $\Delta q_{repo}$ is a 9×1 vector and contains the incremental joint command for joints J1-J9 due to repositioning. Joints J10 and J11 (proximal wrist and distal wrist on the surgical instrument 220) are not involved in this motion. When joints J6-J11 receive additional commands due to teleoperation ($\vec{\Delta q}_{teleop}$), the two commands ($\vec{\Delta q}_{teleop}$ and $\vec{\Delta q}_{repo}$) are summed up to satisfy (1) workspace requirement, (2) insertion-port force requirement, and (3) teleoperation commands at the same time. J1-J5 are not involved in performing the teleoperation commands, so their rows are shown as zeros in $\vec{\Delta q}_{teleop}$. The resulting joint command vector for the entire robot (J1-J11) is given by:

$$\vec{\Delta q} = \begin{bmatrix} \vec{\Delta q}_{repo} \\ 0 \\ 0 \end{bmatrix} + \begin{bmatrix} 0 \\ 0 \\ 0 \\ 0 \\ \vec{\Delta q}_{teleop} \end{bmatrix}$$

Other command or control functions may be used. Other processes for solving for the three sources of movement and positioning may be used.

The selection of the configuration based on workspace alignment, force sensing for RCM change, and/or teleoperation is performed once or may be repeated. Where repeated (see feedback from act 350 to act 300), the robotic manipulator 122 is moved to the selected positions and corresponding configurations over time.

Before starting teleoperation, the robotic surgical system 120 guides the operator to bring the robotic manipulator 122 to the computed "optimal" pose for workspace alignment given the RCM for docking. The guiding is performed quickly and easily based on the computed joint movements ($\vec{\Delta q}$).

The guidance may be performed in a number of different ways. In a haptic guidance via virtual fixtures, active (pseudo-automatic approach) or passive virtual fixtures may be used. In the active approach, on top of user applied force, virtual spring forces are generated to pull the robotic manipulator 122 toward the optimal pose. In this scheme, the manipulator 122 automatically moves toward the optimal pose, but the user can always override or resist the motion by applying counter-force. This allows the user to be kept in the control loop for safety. In the passive approach, the robotic manipulator 122 is not moved automatically but is moved based on the components of the user applied force or torque. The component of the user force or torque toward the optimal pose are amplified while the other components are scaled down. This creates a totally user-driven motion but with a haptic feedback to the user, sensing resistance if trying to move away from the target pose but sensing support if moving toward the optimal pose.

In another guidance, auditory feedback is used. The user is given audio suggestions to bring each joint of the robot to their target position, such as "Rotate joint 1 clockwise." If the target position is overshot, the audio command switches to "rotate joint 1 counterclockwise." Meanwhile, the rest of the joints automatically align themselves to comply with the RCM constraint or force requirement.

In yet another guidance, visual feedback is used. The user is guided through virtual cues to adjust the position of each individual joint. For example, LED status lights on each joint are red if the joint needs to be adjusted. Once the joint reaches the computed position for the "optimal" overall pose, the LED turns green. As another example, an augmented reality display guides the user with arrows superimposed on a view of the actual robot or user input controls.

After starting teleoperation, the same or different guides may be used to adjust the configuration and move the robotic manipulator 122 based on the repositioning of the RCM and/or workspace alignment. Alternatively, the configuration based on workspace alignment and/or RCM force reduction is performed automatically with or without user confirmation to initiate the change.

In an example use case, before starting teleoperation, after the manipulators are docked, the repositioning aid repositions or assists in repositioning the RCM (e.g., pure translate of RCM) so that the stress between the patient and the cannula 214, if any is relieved. The repositioning is also to adjust any one or more of joints J1-J9 in angle to rotate the workspace (i.e., no translation) so that the target anatomy is fully or more in the robot's workspace.

After the teleoperation starts, the workspace requirements may still change, such as due to intraoperative complications, intra-operatively discovered anatomical variations, metastases, deformation or shifting of organs during the surgery, etc. . . . As a result, the new target anatomy may fall out of or be less covered by the boundaries of the previously optimized workspace of the robotic manipulator 122. If such changes in the required anatomical workspace are sensible (e.g., endoscope images combined with joint angles can tell where the surgeon is trying to reach and instrument joints reach their limits but the surgeon is not being able to reach the anatomy to operate), the overall manipulator pose may be continually or periodically reoriented so that the target anatomy is maintained within the reachable workspace of the instrument 220. The reorienting may be triggered to occur, such as by the user. The reorientation allows for continuous teleoperation without having to stop, rethink the arrangement of the anatomy, workspace, and manipulator, then manually bring the manipulators to a new pose, and finally to continue operation. This may prevent loss of operative time.

During the surgery, there may be movement of the tissues as well as the entire patient abdomen. This may induce additional pulling forces on the cannula 214 and cause trauma at the insertion ports on the patient. Extended force application on the patient, like any excess sustained compression of tissues, leads to decreased perfusion of the tissue. Too much force applied to the tissue may impede the capillary blood flow in the skin and also disrupt perforating fascial vessels to the skin. This decreased oxygen delivery to the tissues can be a contributor to incision site hernias and wound-healing complications. Therefore, during the operation, excessive forces at the incision site are prevented or limited by re-adjusting the overall manipulator pose. The forces on the cannula 214 are sensed, and the sensed forces are used as a feedback mechanism for use in the assisted, automatic, or guided repositioning control mode to re-configure the manipulator pose so that the forces at the cannula site are maintained at a tissue-preserving level throughout the surgery.

FIG. 7 shows a block diagram of one embodiment of a surgical robotic system for medical teleoperation. The system performs the method of FIG. 3 or another method. Any one or more (e.g., all) of workspace alignment or force sensing to reposition RCM may be used.

The surgical robot system includes one or more robot manipulators 122 with corresponding surgical instruments 220 or other types of instruments connected with the robotic manipulators 122, a controller 702, and a memory 704. The user console 110 is represented or included as part of the surgical robot system. Additional, different, or fewer components may be provided. For example, the robotic manipulator 122, surgical instrument 220, and/or user console 110 are not provided.

The robotic manipulators 122 each include one or more links and joints. The joints may be pitch or roll joints. A tool drive and cannula 214 for receiving and guiding a surgical tool may be provided on each of the robotic manipulators 122. Different combinations of links and joints may define or form different parts of the robotic manipulators 122, such as different parts having different degrees or types of movement (e.g., translation and/or rotation). Any now known or later develop robotic manipulator 122 with motors, sensors, links, joints, controllers, surgical instruments, and/or other structure may be used.

One or more robotic manipulators 122 are provided. For example, three or four robotic manipulators 122 are provided. The robotic manipulators 122 mount to a table, such as a base of an operating table. Alternatively, cart, floor, ceiling, or other mounts may be used. The robotic manipulators 122 include a cable or wireless transceiver for communication with the controller 702 or an intermediary (e.g., control tower 130).

The robotic surgical instruments 220 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 220 may be mounted to different ones of the robotic manipulators 122. For example, two robotic manipulators 122 may have graspers, a third robotic manipulator 122 may have a scalpel, and a fourth robot manipulator 122 may have an endoscope.

The robotic surgical instruments 220 connect to the distal ends of the robotic manipulators 122 but may connect at other locations. The connection provides a drive so that the tool may be operated, such as closing a grasper or scissors.

The robotic manipulator 122 includes a connected adaptor 420 configured for connecting with the cannula 214 for docking and teleoperation. This connection with the cannula 214 positions the surgical instrument 220 to pass through the cannula 214 at the insertion point for access to the interior of the patient. The insertion point is established as an RCM for the robotic manipulator 122 and surgical instrument 220.

One or more sensors 600 on the cannula and/or on the adaptor 420 monitor the tissue stress for repositioning the RCM. For example, pressure sensors are on different surfaces of the adaptor 420. The different surfaces are ones that contact the cannula 214 when connected. The pressure sensors of the different surfaces of the recess or projection of the adaptor 420 sense one or more degrees of freedom. In combination, a vector of forces is sensed.

The user console 110 is a graphics user interface for interaction of the surgeon with the surgical robot system, such as with a processor for controlling the robotic manipulators 122. The user interface includes a user input 708 and a display 118. The user input 708 and/or the display 118 are provided at the user console 110 and/or control tower 130 but may be at other locations.

The user input 708 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The display 118 is a monitor, liquid crystal display (LCD), projector, plasma display, CRT, printer, or other now known or later developed device for outputting visual information. In an alternative embodiment, the display 118 is a head mounted display. The user input 708 may be a sensor or sensors for detecting eye movement and/or blinking. In yet other embodiments, the user input 708 is a microphone for voice-based input. A speaker for output of audio information may be provided instead of or in addition to the display 118.

The optional camera 706 is a digital camera for optical tracking of user motion, such as tracking during use of the UID 116 to control the robotic manipulator 122. The camera 706 may be a stereo camera and/or depth camera in some embodiments. The camera 706 is positioned relative to a user and a target pattern or user console 110 for tracking human motion in tracing the target pattern or controlling the robotic manipulator 122 with the user input 708.

The controller 702 is a controller that drives and/or models the robotic manipulators 122 and/or surgical instruments 220. The controller 702 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for controlling movement of the robot manipulator 122 and/or surgical instrument 220. The controller 702 is a single device or multiple devices operating in serial, parallel, or separately. The controller 702 may be a main processor of a computer, such as a laptop, server, workstation, or desktop computer, or may be a processor for handling some tasks in a larger system. Based on hardware, software, firmware, or combinations thereof, the controller 702 is configured to implement instructions or perform acts.

The controller 702 is configured to adjust the RCM of the robotic manipulator based on output from the sensor 600. The force at the insertion point, as measured by the sensor 600 (e.g., multiple sensors on adaptor surfaces), is used to alter the RCM to relieve tissue stress.

The controller 702 is configured to determine an amount of overlap between a target anatomy and each of a plurality of workspaces of the surgical instrument. The different workspaces correspond to different positions of the robotic manipulator 122 about the RCM. For a given RCM, different workspaces may be provided by the robotic manipulator 122 having different configurations, such as workspaces with different orientation due to rotation of a joint. The controller 702 is configured to select the position of the robotic manipulator 122 (i.e., select the configuration) with a greatest of the amount of overlap of the workspace with the target anatomy. The controller 702 is configured to move the robotic manipulator to the selected position, such as providing guidance to move the robotic manipulator 122 to the desired configuration. This guidance and corresponding movement may be provided before and/or during teleoperation, such as moving the robotic manipulator 122 to reconfigure for workspace alignment in combination (superposition) with movement for surgical manipulation of the patient by the surgical instrument 220.

The memory 704 or another memory is a non-transitory computer readable storage medium storing data representing instructions executable by the programmed controller 702. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A surgical robotic system for medical teleoperation, the surgical robotic system comprising:
   a robotic manipulator;
   a surgical instrument connected to the robotic manipulator;
   a first sensor configured to measure a force exerted on a body wall of the patient at a remote center of motion;
   an adaptor connected to the robotic manipulator, the adaptor configured to connect with a cannula during teleoperation, and wherein the first sensor is on the adaptor, the cannula for extending through the remote center of motion, wherein the adaptor has a plurality of different surfaces for contact with the cannula, the different surfaces forming a recess in the adaptor, wherein the first sensor is a one-degree-of-freedom sensor on a first of the different surfaces; and
   a controller configured to adjust the remote center of motion of the robotic manipulator based on output from the first sensor.

2. The surgical robotic system of claim 1 further comprising a second sensor on a second of the different surfaces, and wherein the controller is configured to adjust based output from the first and second sensors.

3. The surgical robotic system of claim 2 wherein the controller is configured to select a position of the robotic manipulator and to move the robotic manipulator to the selected position.

4. The surgical robotic system of claim 3 wherein the controller is further configured to move the robotic manipulator to the selected position while providing for movement of the robotic manipulator during teleoperation of the surgical instrument.

5. The surgical robotic system of claim 1 wherein the first sensor is on a part of the robotic manipulator for docking with the cannula.

6. A method for remote center of motion control of a surgical robotic system, the method comprising:
   establishing a remote center of motion for a robotic manipulator;
   selecting a configuration of the robotic manipulator based on an amount of overlap between a target anatomy and a workspace of a surgical instrument on the robotic manipulator, the configuration arranged to maintain the remote center of motion while optimizing the overlap; and
   moving one or more joints of the robotic manipulator to the selected configuration.

7. The method of claim 6 wherein establishing the remote center of motion comprises docking the robotic manipulator to a cannula at an insertion location in a patient, the remote center of motion being the insertion location.

8. The method of claim 6 further comprising sensing a force at the remote center of motion during teleoperation by the robotic manipulator and the surgical instrument; and wherein establishing comprises establishing the remote center of motion from a change based on the force.

9. The method of claim 8 wherein sensing comprises sensing with a sensor on a cannula connected to the robotic manipulator.

10. The method of claim 8 wherein sensing comprises sensing with a force sensor in an adaptor of the robotic manipulator, the adaptor configured to connect the robotic manipulator to a cannula.

11. The method of claim 8 wherein selecting comprises selecting during the teleoperation and wherein moving comprises moving one or more joints of the robotic manipulator to account for the selected configuration and the remote center of motion established in response to the force.

12. The method of claim 11 wherein moving comprises moving the one or more joints to account for the selected configuration, for the remote center of motion established in response to the force, and for movement of the surgical instrument from an operator during the teleoperation.

13. The method of claim 6 wherein selecting comprises determining with the workspace corresponding to a discretized range of joint positions for a spherical roll joint.

14. The method of claim 6 wherein selecting is repeated multiple times during teleoperation, wherein selecting for different ones of the repetitions comprises selecting different workspaces, and wherein moving comprises moving the robotic manipulator to the selected positions over the repetitions.

15. A method for remote center of motion control of a surgical robotic system, the method comprising:
   sensing a force at a remote center of motion of a robotic manipulator; and
   adjusting a joint position of the robotic manipulator, the adjusting (1) reducing the force at the remote center of motion and (2) accounting for another requirement satisfying another operational goal factor in one solution, wherein the other factor comprises an amount of overlap of a workspace of a surgical instrument with a region of interest in the patient.

16. The method of claim 15 wherein adjusting comprises searching different possible workspaces of the surgical instrument for a greatest of the amount of overlap with the region of interest, the possible workspaces corresponding to different possible joint positions of the joint, and selecting the possible workspace with the greatest amount of overlap.

17. The method of claim 15 wherein sensing the force comprises sensing with a force sensor on a cannula connected with the robotic manipulator.

* * * * *

UNITED STATES PATENT AND TRADEMARK OFFICE
CERTIFICATE OF CORRECTION

PATENT NO. : 12,029,514 B2
APPLICATION NO. : 18/075907
DATED : July 9, 2024
INVENTOR(S) : Berk Gonenc et al.

Page 1 of 1

It is certified that error appears in the above-identified patent and that said Letters Patent is hereby corrected as shown below:

In the Claims

Claim 15, Column 18, Lines 66 and 67 "requirement satisfying another operation goal" should be deleted.

Signed and Sealed this
Seventh Day of January, 2025

Derrick Brent
*Acting Director of the United States Patent and Trademark Office*